US00PP28729P3

(12) United States Plant Patent
Wood

(10) Patent No.: US PP28,729 P3
(45) Date of Patent: Dec. 5, 2017

(54) ***HYDRANGEA* PLANT NAMED 'SMHAMWM'**

(50) Latin Name: *Hydrangea arborescence*
Varietal Denomination: SMHAMWM

(71) Applicant: Timothy Wood, Spring Lake, MI (US)

(72) Inventor: Timothy Wood, Spring Lake, MI (US)

(73) Assignee: Spring Meadow Nursery, Inc, Grand Haven, MI (US)

( * ) Notice: Subject to any disclaimer, the term of this patent is extended or adjusted under 35 U.S.C. 154(b) by 23 days.

(21) Appl. No.: 14/998,611

(22) Filed: Jan. 20, 2016

(65) Prior Publication Data

US 2017/0208719 P1 Jul. 20, 2017

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Cassandra Bright

(57) ABSTRACT

A new and distinct *Hydrangea* cultivar named 'SMHAMWM' is disclosed, characterized by large inflorescence, strong flowering stems, bright white blossoms and compact habit. The new variety is a *Hydrangea,* normally produced as an ornamental plant for containers or gardens.

2 Drawing Sheets

Latin name of the genus and species: *Hydrangea arborescence.*

Variety denomination: 'SMHAMWM'.

BACKGROUND OF THE INVENTION

The new *Hydrangea* cultivar is a product of a planned breeding program conducted by the inventor, Timothy D. Wood, in Grand Haven, Mich. The objective of the breeding program was to produce new *Hydrangea* varieties. The cross resulting in this new variety was made during July of 2006.

The seed parent is the unpatented unreleased proprietary variety *Hydrangea arborescence* 'SVG'. The pollen parent is the unpatented commercial variety *Hydrangea arborescence* 'Pink Pincushion'. The new variety was identified as a potentially interesting selection July of 2010, at a greenhouse in Grand Haven, Mich.

Asexual reproduction of the new cultivar 'SMHAMWM' by softwood cuttings was first performed during the June of 2011, at commercial greenhouse in Grand Haven, Mich. Subsequent propagation has shown that the unique features of this cultivar are stable and reproduced true to type in 4 successive generations.

SUMMARY OF THE INVENTION

The cultivar 'SMHAMWM' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMHAMWM' These characteristics in combination distinguish 'SMHAMWM' as a new and distinct *Hydrangea* cultivar:

1. Large inflorescence.
2. Strong flowering stems.

3. Compact plant.
4. Bright white blossoms.

PARENT COMPARISON

Plants of the new cultivar 'SMHAMWM' are similar to plants of the seed parent, unpatented unreleased proprietary variety *Hydrangea arborescence* 'SVG' in most horticultural characteristics, however, plants of the new cultivar 'SMHAMWM' differ in the following:

1. Larger inflorescence.
2. Stronger stems.
3. More floriferous.

Plants of the new cultivar 'SMHAMWM' are similar to plants of the pollen parent, unpatented commercial variety *Hydrangea arborescence* 'Pink Pincushion' in most horticultural characteristics, however, plants of the new cultivar 'SMHAMWM' differ in the following:

1. Larger individual flowers than the pollen parent.
2. White flowers. The pollen parent has pink flowers.
3. Mostly showy flowers with large sepals. The pollen parent has mostly non-showy flowers.

COMMERCIAL COMPARISON

'SMHAMWM' can be compared to the unpatented commercial variety *Hydrangea* 'Annabelle'. These varieties are similar in most horticultural characteristics; however 'SMHAMWM' differs in the following:

1. Hemispherical inflorescence. The comparator has round inflorescence.
2. Stronger stems.
3. Dark green leaves. The comparator has pale green, leaves.

BRIEF DESCRIPTION OF THE PHOTOGRAPHS

Figure 1:
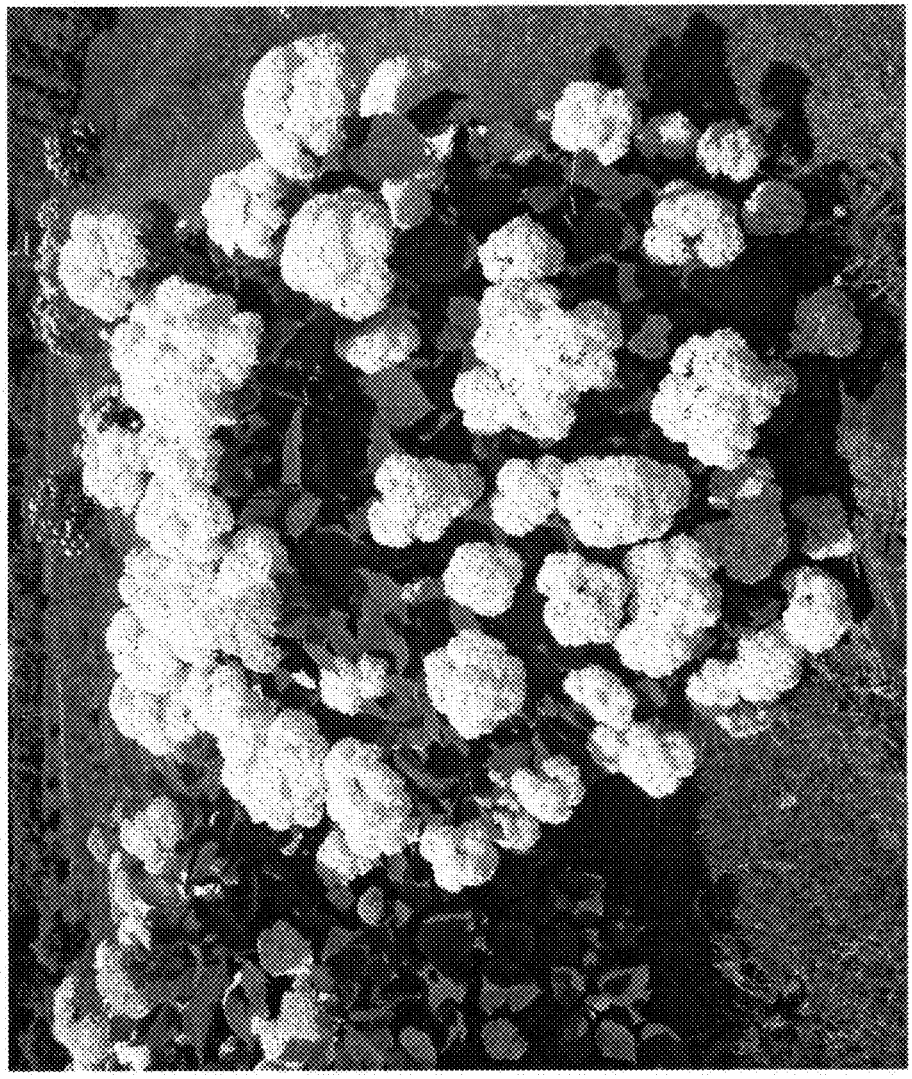

The accompanying photograph in FIG. 1 illustrates in full color a typical mature flowering plant of 'SMHAMWM' grown in a field, in Grand Haven, Mich., USA. Age of the plant photographed is approximately 2-3 years.

Figure 2:
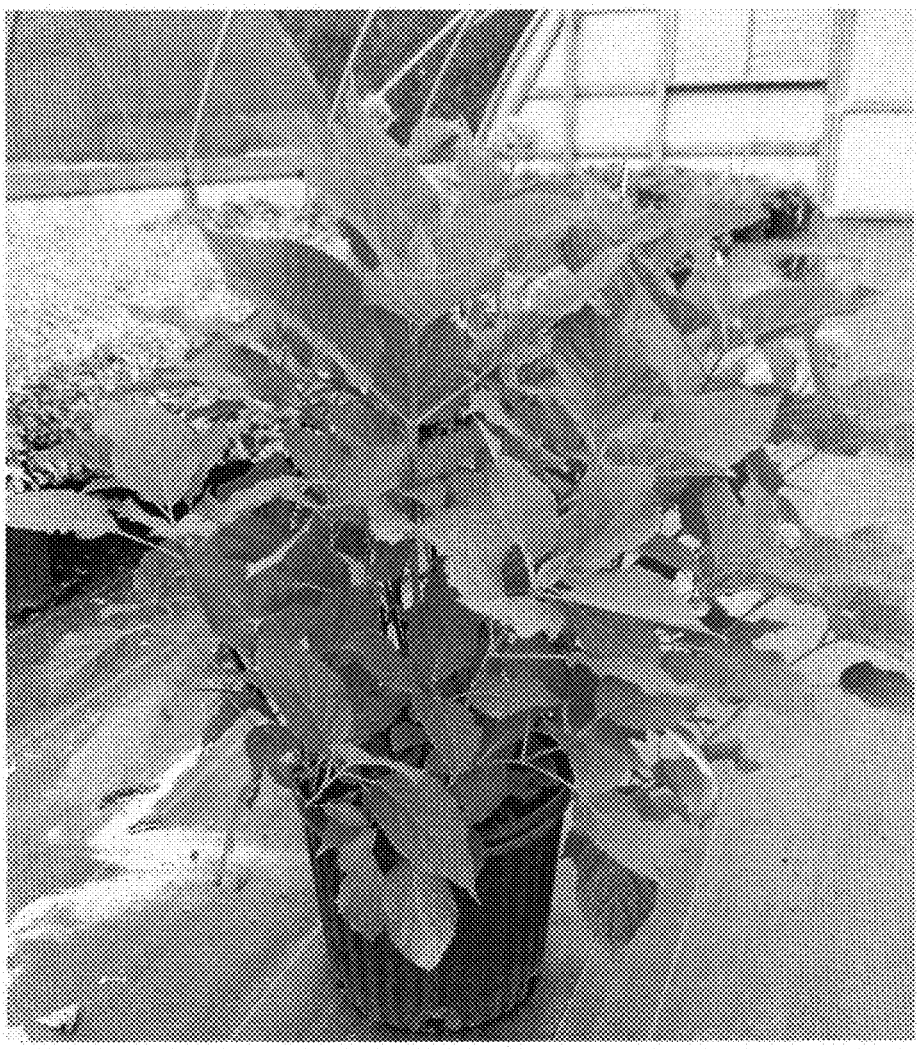

FIG. 2 illustrates a non-flowering plant in a 1 gallon container, at approximately 1 year.

The photographs were taken using conventional techniques and although colors may appear different from actual colors due to light reflectance it is as accurate as possible by conventional photographic techniques.

DETAILED BOTANICAL DESCRIPTION

In the following description, color references are made to The 1996 Royal Horticultural Society Colour Chart except where general terms of ordinary dictionary significance are used. The following observations and measurements describe 'SMHAMWM' plants grown in a double poly greenhouse in Grand Haven, Mich., USA in a 2 gallon pot. The growing temperature ranged from approximately 18° C. to 27° C. daytime and 10° C. at night. Measurements and numerical values represent averages of typical plant types. Measurements were taken during July of 2015.

Botanical classification: *Hydrangea arborescence* 'SMHAMWM.'

PROPAGATION

Time to initiate roots: Approximately 20 days at approximately 24° C.

Time to produce a rooted young plant: Approximately 60 days at approximately 24° C.

Root description: Thin root thickness, high root density, freely root branching, fibrous. Color is white, not accurately measured with R.H.S. chart.

Propagation method: Softwood cuttings.

PLANT

Age of plant described: 2-3 years.
Pot size: 2 gallon.
Growth habit: Flowering perennial shrub, upright/rounded.
Overall plant shape: Upright.
Height: 70 cm.
Plant spread: 50 cm.
Growth rate: Good.
Plant vigor: Good.
Branching characteristics: Basal branches from base or ground level, pinching required.
Length of lateral branches: 50-70 cm.
Number of lateral branches: 25.
Diameter of lateral branches: 6 mm.
Lateral branch shape and appearance: Round.
Lateral branch strength: Good.
Internode length: 9 cm.
Branch color:
- *Immature*.—Near RHS Yellow-green 145C.
- *Mature*.—Near RHS Yellow-green 145A with striations of Greyed-purple 187B.

Branch aspect: Upright.
Branch pubescence: Slight.

FOLIAGE

Leaf:
- *Arrangement*.—Opposite.
- *Average length*.—14.5 cm.
- *Average width*.—10.4.
- *Shape of blade*.—Ovate.
- *Apex*.—Acute.
- *Base*.—Rounded to cordate.
- *Margin*.—Serrate to serrulate.
- *Texture and appearance of top surface*.—Slightly pubescent.
- *Texture and appearance of bottom surface*.—Slightly pubescent.
- *Color*.—Young foliage upper side: Near RHS Green 143B. Young foliage under side: Closest to RHS Green 138C. Mature foliage upper side: Near RHS Green 141B. Mature foliage under side: Near RHS Green 138C.
- *Venation*.—Type: Pinnate. Venation color upper side: Near RHS Yellow-green 146C. Venation color under side: Near Yellow-Green 145B.

Petiole:
- *Average length*.—6.5 cm.
- *Diameter*.—3 mm.
- *Color*.—Upper side: Near RHS Yellow-green 145A with striations of Greyed-purple 187B. Under side: Near RHS Yellow-green 145B.
- *Texture upper side*.—Smooth and pubescent.
- *Texture under side*.—Smooth and pubescent.

FLOWER

Bloom period:
- *Natural season*.—Mid-Summer until Fall.

Inflorescence:
- *Type*.—Mophead.
- *Quantity of flowers per inflorescence*.—Fertile flowers, 50-100. Sterile Flowers, About 1000.
- *Persistent or self-cleaning*.—Persistent.
- *Fragrance*.—Slightly sweet.

Panicle:
- *Shape*.—Semi-orbital to cyme.
- *Height*.—10 cm.
- *Diameter*.—22 cm.

Sterile flower:
- *Androecium*.—Yes.
- *Bud shape*.—Obovate.
- *Bud length*.—2 mm.
- *Bud diameter*.—2 mm.
- *Bud color*.—Near RHS Red-purple 69B.
- *Flower aspect*.—Upright and outward.
- *Flower shape*.—Cruxifix.
- *Flower length*.—2 cm.
- *Flower diameter*.—2 mm.
- *Flower depth*.—2 cm.

Sterile flower petals:
- *Petal arrangement*.—Whorl.
- *Length of petal*.—2 mm.
- *Width of petal*.—1 mm.
- *Apex*.—Acute.
- *Shape of petal*.—Ovate.
- *Petal margin*.—Entire.
- *Petal base*.—Rounded to obtuse.
- *Petal number*.—4.
- *Petal texture*.—Smooth, coriaceous, upper and under side.
- *Color*.—Upper surface at first opening: Near RHS White 155B. Upper surface at maturity: Near RHS White 155B. Under surface at first opening: Near RHS White 155B. Under surface at maturity: Near RHS White 155B.

Sterile flower sepal:
*Arrangement*.—Whorl.
*Number*.—4-5.
*Shape*.—Ovate.
*Tip*.—Acute.
*Base*.—Obtuse.
*Margin*.—Entire.
*Length*.—1 cm.
*Width*.—1 cm.
*Texture, upper*.—Smooth, coriaceous.
*Texture, lower*.—Smooth, coriaceous.
*Color*.—Upper surface at first opening: Near RHS White 155B. Upper surface at maturity: Near RHS White 155B. Under surface at first opening: Near RHS White 155B. Under surface at maturity: Near RHS White 155B. Fading to Upper surface: Near RHS White 155B. Fading to Under surface: Near RHS White 155B.

Sterile flower pedicel:
*Length*.—1 cm.
*Diameter*.—1 mm.
*Angle*.—Upright and outward.
*Strength*.—Good.
*Texture*.—Smooth.
*Color*.—Near RHS Yellow-green 145B.

Fertile flower:
*Bud shape*.—Obovate.
*Bud length*.—2 mm.
*Bud diameter*.—2 mm.
*Bud color*.—Near RHS Red-purple 69B.
*Flower aspect*.—Upright and outward.
*Flower shape*.—Star-like.
*Flower length*.—5 mm.
*Flower diameter*.—5 mm.
*Flower depth*.—4 mm.

Fertile flower petals:
*Length of petal*.—1.5 mm.
*Width of petal*.—1 mm.
*Apex*.—Acute.
*Shape of petal*.—Ovate.
*Petal margin*.—Entire.
*Petal arrangement*.—Whorl.
*Petal number*.—5.
*Petal base*.—Rounded.
*Petal texture*.—Smooth, upper and under side.
*Color*.—Upper surface at first opening: Near RHS White 155B. Upper surface at maturity: Near RHS White 155B. Under surface at first opening: Near RHS White 155B. Under surface at maturity: Near RHS White 155B. Upper surface fading to: Near RHS White 155B. Lower surface fading to: Near RHS White 155B.

Fertile flower pedicel:
*Angle*.—Upright/outward.
*Strength*.—Good.
*Length*.—4 mm.
*Width*.—0.5 mm.
*Texture*.—Smooth.
*Color*.—Near RHS Yellow-green 145A.

Fertile flower sepal:
*Arrangement*.—Whorl.
*Number*.—5.
*Shape*.—Ovate.
*Tip*.—Acute.
*Base*.—Fused.
*Margin*.—Entire.
*Length*.—1 mm.
*Width*.—1 mm.
*Texture, upper*.—Smooth.
*Texture, lower*.—Smooth.
*Color*.—Upper surface at first opening: Near RHS Yellow-green 150C. Upper surface at maturity: Near RHS Yellow-green 150C. Under surface at first opening: Near RHS Yellow-green 150C. Under surface at maturity: Near RHS Yellow-green 150C. Upper surface fading to: Near RHS Yellow-green 150C. Lower surface fading to: Near RHS Yellow-green 150C.

REPRODUCTIVE ORGANS

Sterile flower:
*Stamen number*.—8.
*Filament length*.—0.7 mm.
*Filament color*.—Near RHS White 155B.
*Anther shape*.—Rounded, fusiform.
*Anther color*.—Near RHS Red-purple 65A.
*Anther length*.—1 mm.
*Pollen amount*.—None.
*Gynoecium*.—Yes.
*Pistil number*.—1.
*Pistil length*.—2 mm.
*Stigma shape*.—Blunt.
*Style length*.—1 mm.
*Style color*.—Near RHS Yellow-green 145B.

Fertile flower:
*Stamen number*.—10.
*Filament length*.—1 mm.
*Filament color*.—Near RHS White 155B.
*Anther shape*.—Rounded.
*Anther length*.—1 mm.
*Anther color*.—Near RHS Red-purple 65A.
*Pollen amount*.—Some.
*Pollen color*.—Near RHS White 155B.
*Pistil number*.—2.
*Pistil length*.—2 mm.
*Stigma shape*.—Rounder.
*Stigma color*.—Near RHS Yellow 10D.
*Style length*.—1 mm.
*Style color*.—Near RHS Yellow 10D.
*Ovary color*.—Near RHS Yellow 10D.

OTHER CHARACTERISTICS

Disease resistance: Neither resistance nor susceptibility to diseases or pests has been observed in this variety.

Cold tolerance: −31° C. to 38° C.

Fruit/seed production: 1000's of seeds produced. Abundant, minute seed produced. Seed less than 1 mm in diameter and length, brown, too small to accurately measure with R.H.S. chart.

What is claimed is:

1. A new and distinct cultivar of *Hydrangea* plant named 'SMHAMWM' as herein illustrated and described.

* * * * *